United States Patent [19]

Johnston et al.

[11] Patent Number: 4,954,491

[45] Date of Patent: Sep. 4, 1990

[54] METHOD OF TREATMENT USING 18-CYANOPROGESTERONE DERIVATIVES

[75] Inventors: J. O'Neal Johnston, Milford; Gene W. Holbert, Loveland, both of Ohio

[73] Assignee: Merrell Dow Pharmaceuticals Inc., Cincinnati, Ohio

[21] Appl. No.: 303,367

[22] Filed: Jan. 27, 1989

[51] Int. Cl.$^5$ .......................... A61K 31/57; C07J 9/00; C07J 5/00
[52] U.S. Cl. ...................................... 514/174; 552/556
[58] Field of Search .......................... 260/397.2, 397.45; 514/177; 552/556

[56] References Cited

U.S. PATENT DOCUMENTS 3,092,627  6/1963  Wettstein et al. .................. 260/239
3,684,674  8/1972  Anner et al. ....................... 204/158

FOREIGN PATENT DOCUMENTS 2018252  10/1970  Fed. Rep. of Germany .

OTHER PUBLICATIONS

Viger et al., J. Steroid Biochemistry, 30, 469, 1988.
J. Steroid Biochemistry, 30, 1988, Cover & Preface.
Kalvoda et al., Helv. Chim. Acta, 49, 424(1966).
Kalvoda, Helv. Chim. Acta, 51, 267 (1968).
Kalvoda et al., Helv. Chim. Acta, 52, 2106 (1969).
Kalvoda et al., Helv. Chim. Acta, 55, 356 (1972).
Freerksen et al., J. Am. Chem. Soc., 99, 1536 (1977).
Auel et al., Steroids, 31, 367 (1978).
Holbert et al., Tetrahedron Letters, 26, 1137 (1985).
Viger et al., Tetrahedron, 44, 1127 (1988).
Viger et al., J. Steroid Biochem., 30, 469 (1988).
Chemical Abstracts 74:13344t 1971) (Abstracts of German OLS 2,018,252).
Derwent Abstract 78489R (Abstract of Belgian 749,134; equivalent to U.S. Pat No. 3,684,674).

Primary Examiner—Mukund J. Shah
Assistant Examiner—Deborah D. Carr
Attorney, Agent, or Firm—John J. Kolano

[57] ABSTRACT

The present invention is directed to a method for the treatment of hyperaldosteronism and related disorders which comprises administering to an appropriate patient an appropriate 18-cyanopregnane.

6 Claims, No Drawings

METHOD OF TREATMENT USING 18-CYANOPROGESTERONE DERIVATIVES

BACKGROUND OF THE INVENTION

A. Chemistry

A variety of pregnane compounds having a cyano substituent at the 18-position have been described in the literature. Such compounds can be named as 18-cyanopregnanes or as pregnane-18-carbonitriles. Publications describing compounds of this type include the following:

(1) Kalvoda et al., *Helv. Chim. Acta,* 49, 424 (1966).
(2) Kalvoda, *Helv. Chim. Acta,* 51, 267 (1968).
(3) Kalvoda et al., *Helv. Chim. Acta,* 52, 2106 (1969).
(4) Kalvoda et al., *Helv. Chim. Acta,* 55, 356 (1972).
(5) Freerksen et al., *J. Am. Chem. Soc.,* 99, 1536 (1977).
(6) Auel et al., *Steroids,* 31, 367 (1978).
(7) Holbert et al., *Tetrahedron Letters,* 26, 1137 (1985).
(8) Viger et al., *Tetrahedron,* 44, 1127 (1988).
(9) DE OLS No. 2 018 252 (publ. Oct. 29, 1970).
(10) U.S. Pat. No. 3,092,627 (issued June 4, 1963).
(11) U.S. Pat. No. 3,684,674 (issued Aug. 15, 1972).

As far as specific cyano compounds are concerned, 18cyanoprogesterone (3,20-dioxopregn-4-ene-18-carbonitrile) has been described by Kalvoda et al. (1966), Kalvoda (1968), Auel et al., and U.S. Pat. No. 3,092,627. 18-Cyano-11β-hydroxyprogesterone (11β-hydroxy-3,20-dioxopregn-4-ene-l18carbonitrile) appears to have been described only by Kalvoda et al. (1972) although the corresponding compound in which the 3-ketone is protected as the ethylene ketal (with shifting of the 4-double bond to the 5-position) is described by Holbert et al. 18-Cyanohydrocortisone is described by U.S. Pat. No. 3,684,674 while 18-cyanoprednisolone is described by that same patent and also by Kalvoda et al. (1972). In addition to the specific compounds considered above, many other related compounds are also described in the above publications. Among such other compounds are progesterone derivatives in which one or both of the carbonyl groups are protected as ethylene ketals (with appropriate shifting of any double bond that may be present in the 4-position) or in which a carbonyl group is replaced by a hydroxy group (again with appropriate shifting of any double bond that may be present in the 4-position) The hydroxy group can optionally be further esterified or etherified to give compounds such as a 3-acetate, a 3-t-buty-l ether or a 3-(t-butyl)dimethylsilyl ether. Additionally described in the indicated articles are compounds which do not contain a double bond in the A- or B-ring, compounds which contain an 11-oxo substituent, and also compounds containing both an 11β-hydroxy and a 9α-fluoro substituent.

All of the above publications describe the cyano compounds as intermediates in the preparation of other compounds. In only one case was there any indication that the cyano compounds had been tested for pharmacological activity. Thus, Auel et al. indicated that 18-cyanoprogesterone was tested in the Clauberg and anti-Clauberg tests (in rabbits) and found to be inactive. Otherwise, it is noted that DE No. 2 018 252 and U.S. Pat. No. 3,684,674, which are equivalent patents and which only describe compounds having a 17-hydroxy substituent, contain an assertion of pharmacological activity only with regard to final products obtained from intermediates containing a cyano substituent at the 18-position. However, it is noted that the C. A. abstract of the German patent and the Derwent abstract of the corresponding Belgian patent appear to contain incorrect indications that the cyano compounds possess pharmacological activity. That is, properties which the patents themselves attribute only to the final products described therein have been incorrectly attributed to cyano intermediates for those final products.

B. Utility

Aldosterone is a steroidal hormone which is synthesized in the zona glumerulosa cells of the adrenal glands. The primary biological function of this compound is the regulation of salt retention and, in particular, aldosterone plays a major role in controlling the reabsorption of sodium ions from the urine by the kidney. Thus, a deficiency of the enzyme responsible for the synthesis of aldosterone is a characteristic of patients with a salt-losing syndrome, while primary hyperaldosteronism can result from hyperbiosynthesis of aldosterone as caused by an adrenocortical tumor or the administration of certain drugs. The hyperaldosteronism may involve hypertension, hypokalemia, alkalosis, muscular weakness, polyuria and polydipsia. Thus, treatment of hyperaldosteronism and the conditions associated with it would be possible by blockage of the enzymatic synthesis of aldosterone.

SUMMARY OF THE INVENTION

The present invention relates to the use of certain 18-cyano derivatives of progesterone as aldosterone inhibitors.

DETAILED DESCRIPTION OF THE INVENTION

The present invention relates to a method for treating hyperaldosteronism which comprises administering to a patient having said condition a therapeutically effective amount of an 18-cyanopregnane of the formula

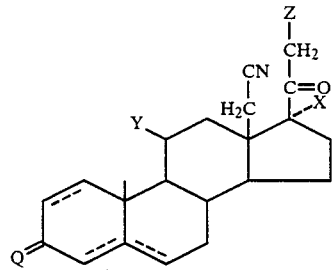

wherein X is H or OH; Y is H, OH or O($C_{2-6}$ Alkanoyl); Z is H, OH or O($C_{2-6}$ Alkanoyl); Q is 0, β-OH or β-O($C_{2-6}$ Alkanoyl); and the dotted lines indicate the optional presence of a double bond with the dotted lines showing optional double bonds at the 4- and 5-positions being selected in such a way that a maximum of one of those dotted lines is a double bond and that double bond is located at the 4-position when Q is 0 and at the 5-position when Q is β-OH or β-O($C_{2-6}$ Alkanoyl); and the hydrogen at the 5-position is α or β when no double bond is present. Examples of the $C_{2-6}$ alkanoyl groups referred to above are acetyl, propionyl, butyryl, isobutyryl and hexanoyl. A preferred embodiment of the present invention relates to a method for treating hyperaldosteronism which comprises administering to a patient having said condition 18-cyanoprogesterone or 18-cyano-11β-hydroxyprogesterone.

More specifically, the present invention relates to the use of the indicated compounds to inhibit the synthesis of aldosterone and thus for use in a method for the treatment of conditions in which such inhibition would be desired. Thus, the indicated compounds are useful in a method for the treatment of hyperaldosteronism and various conditions wherein a reduction of the excessive amount of aldosterone responsible for the condition would be beneficial. That is, they are useful in a method for the general treatment of hyperaldosteronism and any associated hypertension, edema and/or sodium retention whether this is the result of some bodily disorder or whether it results from the administration of some agent. As a result of their effect on the factors responsible for edema and/or sodium retention, the indicated compounds would be useful in a method for treatment as diuretic agents.

The activity of the indicated compounds as aldosterone inhibitors and, thus, their utility in a method for treating hyperaldosteronism can be demonstrated by the following procedure which measures the inhibition of enzymes in the synthesis of aldosterone.

Young male Sprague-Dawley rats were maintained on a sodium-deficient diet for about two weeks prior to use. From these animals, adrenal capsule/glomerulose homogenates were prepared (6 mg/ml) in pH 7.4 assay buffer [$MgCl_2$ 8.5 mM, $CaCl_2$ 2.7 mM, KCl 3.13 mM, NaCl 7.591 mM, TRIS 50 mM and 0.1% triethylamine-]and centrifuged 500xg for 10 minutes.

Assays were conducted in 35 ml glass tubes maintained at 25° C. in a Dubnoff shaker with 95% $O_2$/5% $CO_2$. The tubes contained the following material: 100 μl of an $NADPH^+$generating system, 300 μl of adrenal capsular/glomerulosa cytosol, and 50 μl of test compound or buffer (control). After initial preincubation intervals of 20 minutes, the 10-minute assay was started by the addition of 50 μl of tritium-labelled substrate, i.e., 1 μM [$^3H$]-DOC. Reactions were quenched by the addition of 5 ml of ethyl acetate and non-radiolabelled steroids were also added. The samples were extracted twice with 5 ml of ethyl acetate and the solvent evaporated under nitrogen at 30°–40° C.

Residues were redissolved in methanol:water (40:60) with 0.1% triethylamine and high performance liquid chromatography was used to separate products on a C18 reverse phase (5 μ ODS-Hypersil) column (4.6×250 mm, Shannon) with a 1 ml/min flow rate using an MeOH:$H_2O$ gradient (solvent A 10/90:solvent B 90/10).

Unchanged substrate and products formed were monitored by UV absorbance at 246 nM and the amount of steroid compound present was quantified by [$^3H$]radioactivity. Using this procedure, the following results were observed:

| Test Compound | Conc (μM) | f moles/min/mg | % Inhibition |
| --- | --- | --- | --- |
| Buffer (control) | | 246 | — |
| 3,20-Dioxopregn-4-ene-18-carbonitrile | 10 | 117 | 52.5 |
| 11β-Hydroxy-3,20-dioxopregn-4-ene-18-carbonitrile | 10 | 164 | 33.3 |

The above results demonstrate the effectiveness of 18-cyanopregnanes as inhibitors of aldosterone biosynthesis according to the method of the present invention.

To achieve a particular desired effect, such as a diuretic effect, in the method of the present invention, the compounds as described above can be administered orally or parenterally, for example, intramuscularly and subcutaneously, to a patient in need of treatment. The term patient is taken to mean a warm-blooded mammal such as rats, mice, dogs, cats, horses, pigs, cows, sheep and humans. The compounds of the invention can be administered alone or suitably admixed in the form of a pharmaceutical preparation to the patient being treated. The amount of compound administered will vary with the severity of the condition and repetitive treatment may be desired. For oral and parenteral administration, the amount of compound administered, that is, the diuretic effective amount, is from 0.1 to 150 mg/kg of body weight per day and preferably from 1 to 50 mg/kg of body weight per day. Unit dosages for oral or parenteral administration may contain, for example, from 5 to 200 mg of the active ingredient. The compounds can be administered alone or in combination with one another, or in combination with other diuretics.

For oral administration, the compounds can be formulated into solid or liquid preparations, such as capsules, pills, tablets, troches, powders, solutions, suspensions or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch or gelatin, disintegrating agents such as potato starch or alginic acids and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols, such as, propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic, silicone rubber manufactured by the Dow-Corning Corporation. Sustained release can also be achieved by use of an appropriately formulated transdermal patch.

The following are illustrative pharmaceutical formulations suitable for oral or parenteral administration which may be employed in practicing the present invention:

TABLET

| | | |
|---|---|---|
| (a) | 11β-Hydroxy-3,20-dioxopregn-4-ene-18-carbonitrile | 75.0 g |
| (b) | Lactose | 1.216 kg |
| (c) | Corn starch | 0.3 kg |

Mix the active ingredient, the lactose, and the corn starch uniformly. Granulate with 10% starch paste. Dry to a moisture content of about 2.5%. Screen through a No. 12 mesh screen. Add and mix the following:

| | | |
|---|---|---|
| (a) | Magnesium stearate | 0.015 kg |
| (b) | Corn starch qs ad | 1.725 kg |

Compress on a suitable tablet machine to a weight of 0.115 g/tablet.

IM INJECTIONS (Oil Type)

| | | |
|---|---|---|
| (a) | 11β-Hydroxy-3,20-dioxopregn-4-ene-18-carbonitrile | 25.0 mg |
| (b) | BHA, BHT aa | 0.01 % w/v |
| (c) | Peanut oil or sesame oil qs | 1.0 ml |

What is claimed is:

1. A method for treating hyperaldosteronism which comprises administering to a patient having said condition a therapeutically effective amount of a compound of the formula

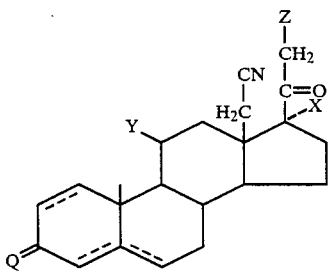

wherein X is H or OH; Y is H, OH or O($C_{2-6}$ Alkanoyl); Z is H, OH or O(C2-6 Alkanoyl); Q is 0, β-OH or β-O($C_{2-6}$ Alkanoyl); and the dotted lines indicate the optional presence of a double bond with the dotted lines showing optional double bonds at the 4- and 5-positions being selected in such a way that a maximum of one of those dotted lines is a double bond and that double bond is located at the 4-position when Q is 0 and at the 5-position when Q is β-OH or β-O($C_{2-6}$ Alkanoyl); and the hydrogen at the 5-position is β or β when no double bond is present.

2. A method according to claim 1 for treating hyperaldosteronism which comprises administering to a patient having said condition a therapeutically effective amount of a compound of the formula

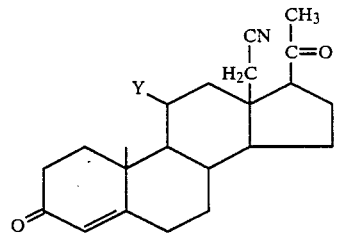

wherein Y is H or OH.

3. A method according to claim 1 for treating hyperaldosteronism which comprises administering to a patient having said condition a therapeutically effective amount of 11δ-hydroxy-3,20-dioxopregn-4-en-18-carbonitrile.

4. A method for producing a diuretic effect which comprises administering to a patient in need of such treatment an effective amount of a compound of the formula

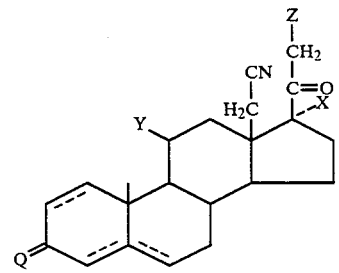

wherein X is H or OH; Y is H, OH or O($C_{2-6}$ Alkanoyl); Z is H, OH or O($C_{2-6}$ Alkanoyl); Q is O, β-OH or β-O($C_{2-6}$ Akanoyl); and the dotted lines indicate the optional presence of a double bond with the dotted lines showing optional double bonds at the 4- and 5- positions being selected in such a way that a maximum of one of those dotted lines is a double bond and that double bond is located at the 4-position when Q is O and at the 5-position when Q is β-OH or βO($C_{2-6}$ Akanoyl); and the hydrogen at the 5-position is a α or β when no double bond is present.

5. A method according to claim 4 for producing a diuretic effect which comprises administering to a patient in need of such treatment a therapeutically effective amount of a compound of the formula

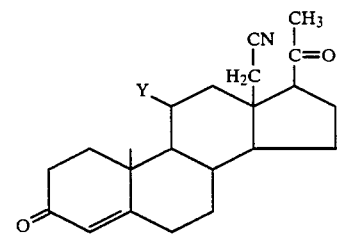

wherein Y is H or OH.

6. A method according to claim 4 for producing a diuretic effect which comprises administering to a patient in need of such treatment a therapeutically effective amount of 11β-hydroxy-3,20-dioxopregn-4-ene-18-carbonitrile.

* * * * *

UNITED STATES PATENT AND TRADEMARK OFFICE
CERTIFICATE OF CORRECTION

PATENT NO. : 4,954,491

DATED : September 4, 1990

INVENTOR(S) : J. O'Neal Johnston, Gene W. Holbert

It is certified that error appears in the above-identified patent and that said Letters Patent is hereby corrected as shown below:

Column 1, Line 31 patent reads: "-11ßcarbonitrile" and should read ---18-carbonitrile--.

Column 1, Line 50 patent reads: "3-t-buty-1 ether" and should read -- 3-t-butyl ether --.

Column 5, Line 61 patent reads: "is β or β" and should read -- is α or β --.

Column 6, Line 16 patent reads: "11δ-hydroxy...." and should read --11β-hydroxy.... --.

Column 6, Line 37 patent reads: "Akanoyl)" and should read -- Alkanoyl) --.

Column 6, Line 43 patent reads: "βO($C_{2-6}$ Akanoyl);" and should read -- β-O($C_{2-6}$ Alkanoyl); --.

Signed and Sealed this

Seventeenth Day of December, 1991

Attest:

HARRY F. MANBECK, JR.

Attesting Officer

Commissioner of Patents and Trademarks